US012755823B2

(12) United States Patent
Hossain et al.

(10) Patent No.: US 12,755,823 B2
(45) Date of Patent: Oct. 6, 2026

(54) ELECTRONIC DEVICE AND HEALTH MANAGEMENT METHOD USING SAME

(71) Applicant: SAMSUNG ELECTRONICS CO., LTD., Suwon-si (KR)

(72) Inventors: Md. Iqbal Hossain, Suwon-si (KR); Jakia Sultana, Suwon-si (KR); Shaswati Saha, Suwon-si (KR); Ummey Habiba Bristy, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 127 days.

(21) Appl. No.: 18/106,228

(22) Filed: Feb. 6, 2023

(65) Prior Publication Data

US 2023/0187043 A1 Jun. 15, 2023

Related U.S. Application Data

(63) Continuation of application No. PCT/KR2021/010233, filed on Aug. 4, 2021.

(30) Foreign Application Priority Data

Aug. 6, 2020 (KR) ........................ 10-2020-0098384

(51) Int. Cl.
*G16H 20/00* (2018.01)
*G16H 10/60* (2018.01)
(Continued)

(52) U.S. Cl.
CPC ............. *G16H 20/00* (2018.01); *G16H 10/60* (2018.01); *G16H 40/67* (2018.01); *G16H 50/30* (2018.01)

(58) Field of Classification Search
CPC ........ G16H 50/30; G16H 10/60; G16H 50/70; G16H 40/60; G16H 40/67; G16H 50/20; G16H 80/00; G16H 15/00
See application file for complete search history.

(56) References Cited

U.S. PATENT DOCUMENTS

2014/0135873 A1 5/2014 An et al.
2015/0250426 A1 9/2015 Muehlsteff
(Continued)

FOREIGN PATENT DOCUMENTS

JP 2015-531261 A 11/2015
JP 2018-5512 A 1/2018
(Continued)

OTHER PUBLICATIONS

Wu, Winston H., et al. "Incremental diagnosis method for intelligent wearable sensor systems." IEEE Transactions on Information Technology in Biomedicine 11.5 (2007): 553-562. (Year: 2007).*
(Continued)

*Primary Examiner* — Constantine Siozopoulos
(74) *Attorney, Agent, or Firm* — Sughrue Mion, PLLC

(57) ABSTRACT

An electronic device comprising: a sensor; a memory; and a first processor, wherein the first processor is configured to: receive first data of a user of the electronic device sensed at preconfigured intervals via the sensor; identify second data comprising location information of the user or information input by the user; compare the first data and the second data with threshold values pre-stored in the memory to generate a result; detect a current health state of the user based on the result; output recommended guide information based on the detected current health state; and re-detect the current health state of the user based on changed first data received at the preconfigured intervals and the second data.

12 Claims, 10 Drawing Sheets

(51) Int. Cl.
*G16H 40/67* (2018.01)
*G16H 50/30* (2018.01)

(56) References Cited

U.S. PATENT DOCUMENTS

| | | | | |
|---|---|---|---|---|
| 2016/0213979 | A1 | 7/2016 | Lee et al. | |
| 2016/0270717 | A1* | 9/2016 | Luna | A61B 5/743 |
| 2017/0310775 | A1 | 10/2017 | Tatourian et al. | |
| 2018/0246570 | A1 | 8/2018 | Coleman et al. | |
| 2018/0268735 | A1 | 9/2018 | Jihn | |
| 2018/0279900 | A1 | 10/2018 | Moghaddam | |
| 2019/0252079 | A1* | 8/2019 | Constantin | A61B 5/7275 |
| 2020/0093988 | A1* | 3/2020 | Zhong | A61M 5/1723 |

FOREIGN PATENT DOCUMENTS

| | | | | |
|---|---|---|---|---|
| KR | 10-1502765 B1 | 3/2015 | | |
| KR | 10-1633344 B1 | 6/2016 | | |
| KR | 10-2016-0091694 A | 8/2016 | | |
| KR | 10-2018-0068917 A | 6/2018 | | |
| KR | 10-1941273 B1 | 4/2019 | | |
| KR | 10-2019-0081941 A | 7/2019 | | |
| WO | WO-2018057507 A1 * | 3/2018 | | A61B 5/0022 |

OTHER PUBLICATIONS

Communication dated Nov. 11, 2021, issued by the International Searching Authority in counterpart International Application No. PCT/KR2021/010233 (PCT/ISA/210).

Communication dated Nov. 11, 2021, issued by the International Searching Authority in counterpart International Application No. PCT/KR2021/010233 (PCT/ISA/237).

Communication dated Apr. 10, 2025, issued by the Korean Patent Office in Korean Application No. 10-2020-0098384.

Office Action issued Dec. 11, 2025 by the Korean Ministry of Intellectual Property for KR Patent Application No. 10-2020-0098384.

* cited by examiner

ELECTRONIC DEVICE AND HEALTH MANAGEMENT METHOD USING SAME

CROSS-REFERENCE TO RELATED APPLICATIONS

This application is a by-pass continuation application of International Application No. PCT/KR2021/010233, filed on Aug. 4, 2021, which is based on and claims priority to Korean Patent Application No. 10-2020-0098384, filed on Aug. 6, 2020, in the Korean Intellectual Property Office, the disclosures of which are incorporated by reference herein in their entireties.

BACKGROUND

1. Field

One or more embodiments of the disclosure relate to an electronic device and a health management method using the same.

2. Description of Related Art

Various electronic devices are used in everyday life. For example, portable terminals, represented by smartphones, and wearable devices (e.g., a smart watch) are closely related and used, and medical diagnostic devices are also popular and used at home.

Research is underway to manage health through electronic devices using a life pattern, health information, and location information of a user. It is possible to check the user's health through a portable terminal, such as a smartphone, and provide information suggesting to maintain the best condition.

Health-related data collected by an electronic device may vary depending on the external environment of the user who uses the electronic device. Such data may be obtained through diagnosis using the electronic device or may be integrated into external cloud data and then received.

Data collected through electronic devices used in various environments may include health states of individual users. Data of users in the same or similar environment may be helpful in providing guidance on health care to individual users.

SUMMARY

An electronic device comprising: a sensor; a memory; and a first processor, wherein the first processor is configured to: receive first data of a user of the electronic device sensed at preconfigured intervals via the sensor; identify second data comprising location information of the user or information input by the user; compare the first data and the second data with threshold values pre-stored in the memory to generate a result; detect a current health state of the user based on the result; output recommended guide information based on the detected current health state; and re-detect the current health state of the user based on changed first data received at the preconfigured intervals and the second data.

A method of operating an electronic device, the method comprising: receiving first data of a user of the electronic device sensed at preconfigured intervals via a sensor; identifying second data comprising location information of the user or information input by the user; comparing the received first data and the identified second data with threshold values; based on the comparing, detecting a current health state of the user; outputting recommended guide information based on the detected current health state; and re-detecting the current health state of the user based on changed first data received at the preconfigured intervals and the second data.

An electronic device and a health management method using the same according to one or more embodiments of the disclosure may provide a guide for maintaining the best condition by checking the health state of a user of each electronic device.

In addition, the electronic device may collect health data on users of similar or identical ages, genders, preferences, and the like living in similar or identical environments and derive action guidelines suitable for respective users.

BRIEF DESCRIPTION OF THE DRAWINGS

Other aspects, advantages and salient features of the disclosure will become apparent to those skilled in the art from the following detailed description, which, taken in conjunction with the accompanying drawings, discloses one or more embodiments of the disclosure.

It will be understood that like reference numerals refer to like parts, components, and structures throughout the drawings.

DETAILED DESCRIPTION

The following description with reference to the accompanying drawings is provided to assist in a comprehensive understanding of one or more embodiments of the disclosure as defined by the claims and their equivalents. It includes one or more specific details to assist in that understanding but these are to be regarded as merely exemplary. Accordingly, those of ordinary skill in the art will recognize that one or more changes and modifications of the one or more embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of one or more embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
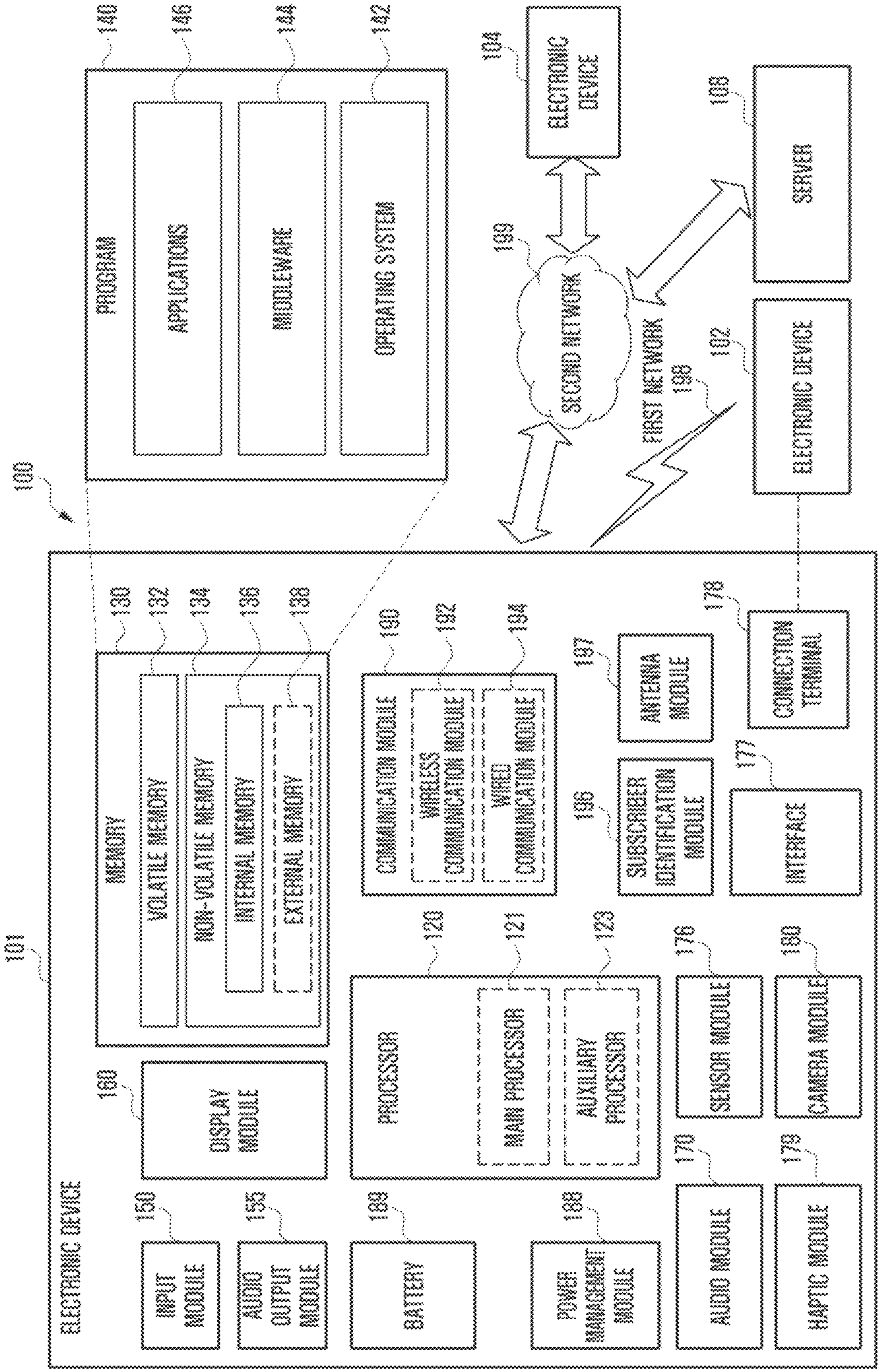
FIG. 1 is a block diagram of an electronic device in a network environment, according to one or more embodiments.

FIG. 1 is a block diagram illustrating an electronic device in a network environment according to an embodiment of the disclosure.

Referring to FIG. 1, an electronic device 101 in a network environment 100 may communicate with an electronic device 102 via a first network 198 (e.g., a short-range wireless communication network), or at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN))). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4th generation (4G) network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the millimeter wave (mmWave) band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 (e.g., the wireless communication module 192) from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
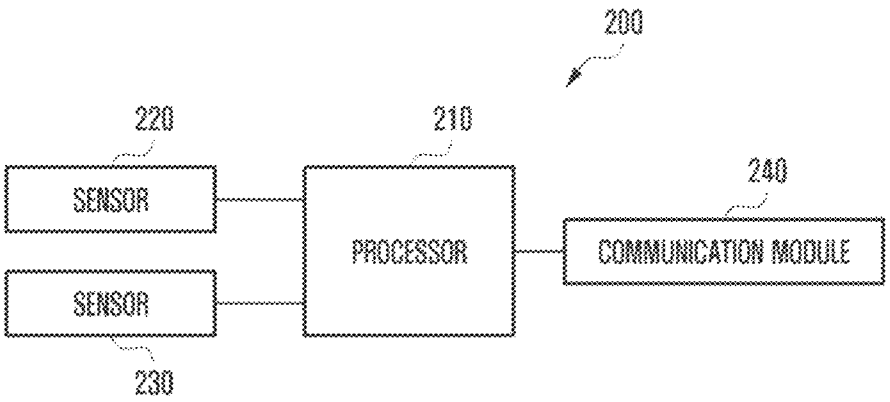
FIG. 2 is a block diagram illustrating the configuration of an electronic device according to one or more embodiments.

FIG. 2 is a block diagram illustrating the configuration of an electronic device according to one or more embodiments.

Referring to FIG. 2, an electronic device 200 (e.g., the electronic device 101 in FIG. 1) may include a processor 210, a sensor 220, a memory 230, and a communication module 240, and some of the illustrated elements may be omitted or substituted. The electronic device may include at least some of the configurations and/or functions of the electronic device 101 in FIG. 1.

According to one or more embodiments, the processor 210 (e.g., the processor 120 in FIG. 1) is an element capable of performing an operation or data processing related to control and/or communication of elements of the electronic device, and may include at least some of the configurations and/or functions of the processor 120 in FIG. 1. The processor 210 may be functionally, operatively, and/or electrically connected to elements inside the electronic device, including the sensor 220, the memory 230, and the communication module 240

The sensor 220 (e.g., the sensor module 176 in FIG. 1) according to one or more embodiments may sense a health state of a user of the electronic device. For example, the sensor 220 may include a biometric sensor, a temperature sensor, a humidity sensor, and the like. The element of sensor 220 may be omitted or substituted, and may include at least some of the configurations and/or functions of the sensor module 176 in FIG. 1.

Referring to FIG. 2, the memory 230 (e.g., the memory 130 in FIG. 1) may be functionally, operatively, and/or electrically connected to the processor and store various instructions capable of being executed by the processor. The instructions may include one or more control commands including arithmetic and logical operations, data transfer, and input/output that may be recognized by the processor. The memory according to one or more embodiments of the disclosure may include at least some of the configurations and/or functions of the memory 130 in FIG. 1.

The communication module 240 (e.g., the communication module 190 in FIG. 1) according to one or more embodiments may support performing communication, including a wireless communication channel, for data sharing between the electronic device and an external device. The communication module may be operated independently of the processor, or may be connected thereto and operated together, and may include at least some of the structures and/or functions of the communication module 190 in FIG. 1.

Figure 3:
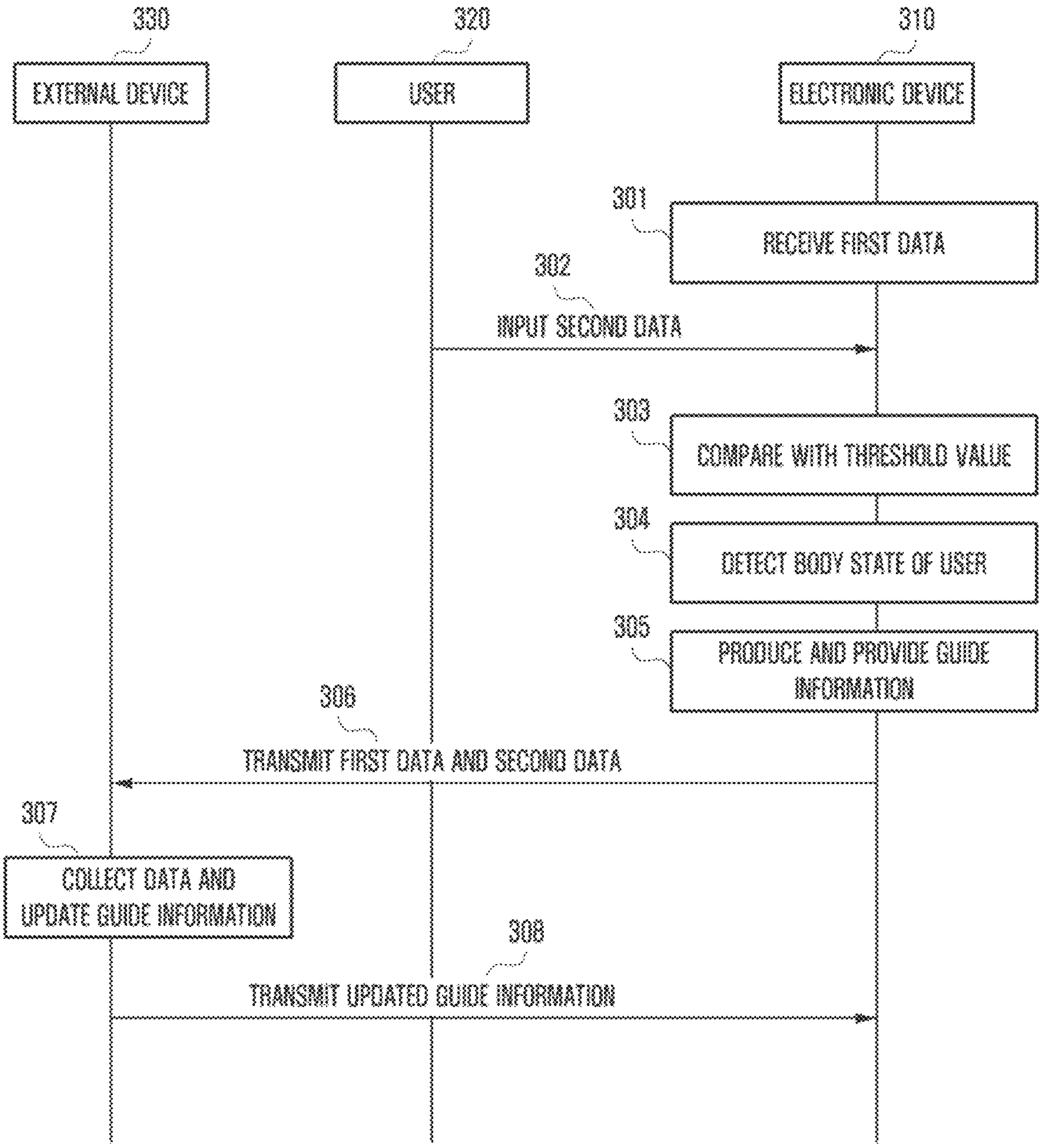
FIG. 3 is a flowchart of checking a health state of a user of an electronic device and providing guide information according to one or more embodiments.

FIG. 3 is a flowchart of checking a health state of a user of an electronic device and providing guide information according to one or more embodiments.

Referring to FIG. 3, an electronic device 310 may include at least some of the structures and/or functions of the electronic device 101 in FIG. 1 and/or the electronic device 200 in FIG. 2. The electronic device 310 may receive first data 301 at preconfigured intervals. Here, the first data may include biometric information of a user sensed through a sensor of the electronic device, biometric information of a user sensed or collected by an external device (e.g., a wearable device, a medical diagnostic device, etc.), and like. According to one or more embodiments, the first data may include user's EEG-related information measured by electroencephalography (EEG), measurement information by functional near-infrared spectroscopy (fNIRS), and the like.

Referring to FIG. 3, the electronic device 310 may receive and identify second data including information input by the user 302. For example, the second data may include the real-time location of an electronic device user, weather and temperature at the real-time location, eating habits of the electronic device user, body information thereof, and the like. In addition, the second data may be comprised of information other than the first data that may be sensed or collected, and may relate to information corresponding to threshold values pre-stored in the electronic device.

The processor of the electronic device may be configured to receive and update the first data and the second data at preconfigured intervals. The interval for receiving the first data and the second data may be determined in order to detect a health state by updating biometric information of the electronic device user in real time.

Referring to FIG. 3, the processor may be configured to compare the first data and the second data with threshold values pre-stored in the memory of the electronic device

303. The pre-stored threshold values may relate to numerical values capable of representing a health state in a normal range corresponding to information of the first data and the second data.

The processor (e.g., the processor 120 in FIG. 1 or the processor 210 in FIG. 2) of the electronic device may detect a health state of the electronic device user according to a result of comparison with the threshold value 304. The processor may be configured to produce pre-stored recommended guide information and provide the same to the user, based on the detected health state. According to an embodiment, the processor may compare a sensed amount of body fluid of the user with a threshold value to determine the current user health state of insufficient fluid. In this case, the processor may be configured to recommend guide information related to "rehydration" from among the pre-stored recommended guide information. According to another embodiment, the processor may compare a user's heart rate with a threshold value to determine that the current user health state is an abnormal state (e.g., excited state). In this case, the processor may be configured to recommend guide information related to "heart rate normalization" from among the pre-stored recommended guide information.

The guide information provided by the electronic device may be pre-stored in the electronic device, or may be updated by an external device and then received therefrom. In addition, producing and providing the guide information 305 may be also performed through the electronic device itself or a display of an external device if the user is able to recognize the same through the display.

The electronic device may transmit the received first data and second data to the external device 306. For example, in order to produce guide information according to health states of a plurality of electronic device users, the external device may collect a plurality of pieces of information and update the guide information 307. Updating the guide information in the external device may be intended to provide an optimized guide to each electronic device user, based on a variety of data. For example, if data on a large amount of activity is accumulated and collected for men, based on data of users in their late teens, it may be updated to produce and provide guide information on nutrition. As another example, if data on nutrition intake is accumulated and collected based on data of users who are pregnant, it may be updated to produce and provide guide information for recommending meals further based on the eating habits of respective users.

The external device may transmit the updated and produced guide information to the electronic device 308. The electronic device may receive the updated guide information and provide guide information corresponding to the first data and second data of the electronic device user.

Figure 4:
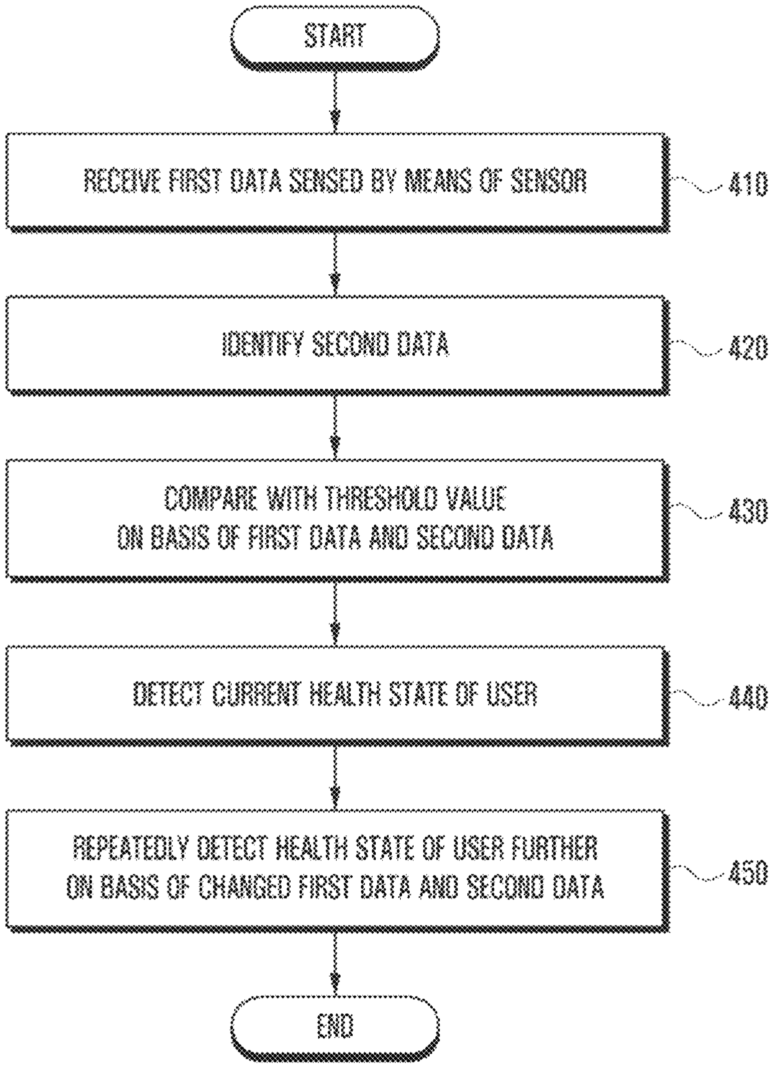
FIG. 4 is a flowchart illustrating a health care method according to one or more embodiments.

FIG. 4 is a flowchart illustrating a health care method according to one or more embodiments.

Referring to FIG. 4, a processor (e.g., the processor 120 in FIG. 1 or the processor 210 in FIG. 2) may receive first data sensed by a sensor 410. Here, first data may not indicate one type of data. For example, the first data may include biometric information of an electronic device user. According to an embodiment, the user's biometric information may include a heart rate, an electrocardiogram, stress, and the number of steps. The biometric information of the electronic device user may be sensed by a sensor and may be collected by other measuring means and/or sensing means other than the sensor.

The first data may include biometric data of each user of the electronic device (e.g., the electronic device 101 in FIG. 1 or the electronic device 200 in FIG. 2). For example, the first data may include information related to all bio-activities capable of being collected while the user carries the electronic device and acts. According to an embodiment, the processor may receive the user's biometric information sensed by a sensor provided inside the electronic device or collected by a biometric information collection module provided therein. According to another embodiment, the processor may further receive first data from an external device. In this case, information such as body temperature, blood pressure, blood oxygen concentration, blood carbon dioxide concentration, and the amount of body fluid of the electronic device user, which may be measured by an external device (e.g., a wearable device, a medical diagnostic device, etc.) may be received through the communication module. The first data configured to be received by the processor of the electronic device is not limited to the above examples, and may be anything related to the quantity that may be an index for determining the user's health state using the external device.

Referring to FIG. 4, the processor may be configured to identify second data 420. Here, the second data may include the real-time location of an electronic device user, weather at the real-time location, temperature at the real-time location, eating habits of the electronic device user, body information of the electronic device user, and the like. According to an embodiment, the user of the electronic device may input information about the user's age, gender, chronic disease, etc. into the electronic device, and this may be included in the second data. According to another embodiment, the second data may include information other than the user's biometric information that may be sensed or collected by the electronic device itself. The second data may include information for determining a health value according to age, gender, etc., and may be data having values to be compared with threshold values pre-stored in the electronic device.

Referring to FIG. 4, the processor may compare the first data and second data with threshold values pre-stored in the electronic device 430. For example, the electronic device may pre-store threshold values corresponding to normal ranges of items for checking the user's health state according to a category of the first data and the second data or a predetermined classification. Here, the pre-stored threshold values may include values in normal ranges of biometric information statistically based on the age, gender, etc. of the electronic device user.

Referring to FIG. 4, the processor may detect the current health state of the electronic device user by comparing the first data and second data sensed at preconfigured intervals with threshold values 440. For example, the processor may compare the first data obtained by quantifying the sensed biometric information of the user and the second data according to the user's body information, age, location, and external environment with threshold values, thereby detecting the current user health state. According to an embodiment, the processor may compare the amount of body fluid of the user sensed by the external device with a threshold value to determine the current user health state of insufficient fluid. According to another embodiment, the processor may compare a user's heart rate sensed by the external device with a threshold value to determine that the current user health state is an abnormal state (e.g., excited state).

Referring to FIG. 4, the processor may be configured to repeatedly detect the user's health state further based on the first data and second data that change at preconfigured intervals 450. For example, the user's health state may change in real time, and the processor may repeatedly detect the user's health state by periodically sensing and identifying the first data and the second data.

Figure 5:
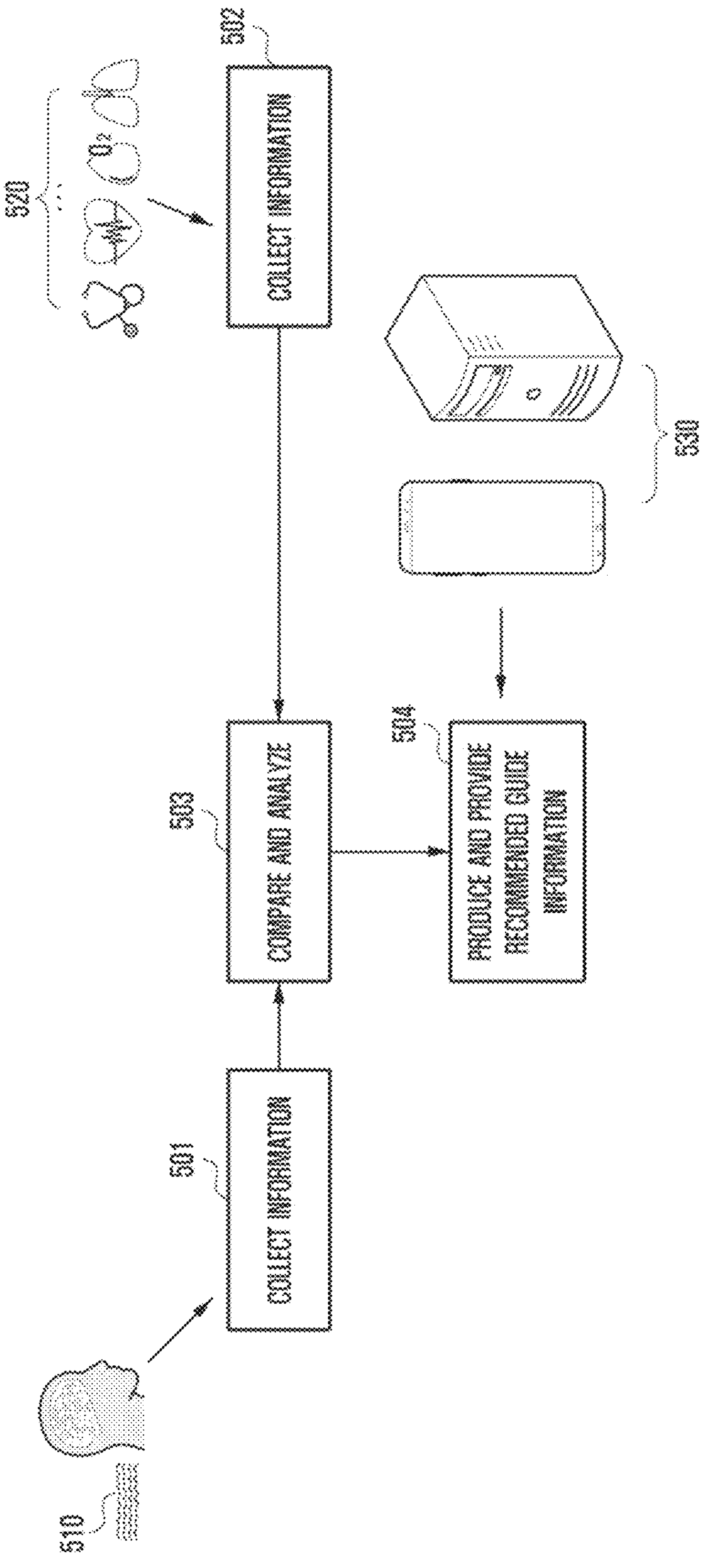
FIG. 5 is a flowchart illustrating an operation of receiving health-related data from an external device of an electronic device and presenting activities according to one or more embodiments.

FIG. 5 is a flowchart illustrating an operation of receiving health-related data from an external device of an electronic device and recommending activities according to one or more embodiments.

Referring to FIG. 5, information 510 and 520 on first data may be collected from external devices in operations 501 and 502. The first data may include EEG-related data. The EEG-related data may be measured from an external device (e.g., an electroencephalograph) capable of being worn on the electronic device user. The electronic device may be configured to receive the measured EEG-related data through communication connection with the external device.

According to an embodiment, the EEG-related data may be measured in an invasive way. For example, the invasive way may be a method in which an EEG measuring needle or the like is invasive to the scalp of the electronic device user to measure EEG. According to another embodiment, the EEG-related data may be measured in a non-invasive way. For example, the non-invasive way may be a method of measuring EEG while being worn on the head of the user of the electronic device.

Referring to FIG. 5, information related to the first data capable of being collected by the electronic device may include data other than EEG. Information related to the first data may be measured and/or received from one or more external devices and/or electronic devices. In operation 503, the processor of the electronic device may be configured to compare and analyze threshold values corresponding to the measured and/or received first data. In operation 504, recommended guide information may be produced and provided from the electronic device and/or a server 530.

Information related to the first data measured by external devices may include EEG (e.g., sensorimotor rhythm (SMR)), regional cerebral blood flow (rCBF), levels of neurotransmitter, heart rate, stress, blood pressure, blood oxygen concentration, blood carbon dioxide concentration, and the like.

According to an embodiment, it is possible to determine a mental situation of the electronic device user, based on the first data measured by the external device. For example, determination indexes such as depression or hopelessness may be used as the first data. Measurement information such as blood oxygen (or carbon dioxide) concentration, levels of neurotransmitter, brain wave gamma coupling, heart rate, blood pressure, etc. may be collected and used as the first data. According to another embodiment, an operation of comparing average data of ages of the electronic device users with the first data may be performed. The average data of first data-related parameters corresponding to the age of the user may be utilized as a threshold value for comparison with the first data collected to determine the user's mental state. For example, the processor of the electronic device may compare the values of individual parameters of the data preconfigured as threshold values with the measured first data, thereby determining the user's mental state.

According to an embodiment, the processor of the electronic device may suggest a recommended action related to the user's action guideline, based on the first data measured by the external device. For example, if it is determined that the user is in a depressed state, the processor may suggest a recommended action related to the corresponding state. According to another embodiment, the depressed state may reflect values such as EEG information, blood flow, blood oxygen concentration, and the like. The processor may suggest "light running" as a recommended action to enable alteration of EEG, alteration of blood flow to a normal range, and alteration of blood oxygen concentration to a normal range.

According to an embodiment, a state (e.g., obesity) related to the degree of obesity of the electronic device user may be determined based on the first data measured by an external device. For example, it may be determined whether or not a sweet food is desired through the first data. The processor may analyze the current user weight, blood sugar level, etc. to determine the degree of obesity and sense EEG generated due to information on the food visually identified or the like. The processor may be configured to suggest other foods or alternatives (e.g., water) to encourage refraining from consuming high-calorie foods.

According to an embodiment, the dehydration state of the electronic device user may be determined based on the first data measured by the external device. For example, parameters indicative of dehydration may include heart rate, tissue oxygenation, arterial oxygenation, skin perfusion, total hemoglobin concentration, intervals between heart beats, tissue water absorption, skin temperature, core temperature, intervals between breaths, depth of breath, and the like. According to another embodiment, the processor may determine that the user is dehydrated. For example, the processor may determine that the user is in the dehydration state if the heart rate increases, if the tissue oxygenation decreases, if the arterial oxygenation decreases, if the skin perfusion decreases, if the total hemoglobin concentration increases, if the intervals between heart beats decrease, if the tissue water absorption decreases, if the skin temperature increases, if the core temperature decreases, if the intervals between breaths decrease, and if the depth of breath decreases. The processor may suggest "rehydration" to the user as a recommended action to recover from the dehydration.

According to an embodiment, caffeine intake of the electronic device user may be determined based on the first data measured by the external device. For example, the electronic device user may consume 200 mg of coffee. The processor may identify an increase or decrease of HbR and HbO from the blood oxygenation level-dependent. An increase in HbO and a decrease in HbR may be identified from the left brain of the user due to an intake of 200 mg of coffee. In addition, a decrease in regional cerebral blood flow and an increase in activity of the automatic nervous system may be identified. The processor may sense a decrease in blood flow, an increase in peripheral resistance, an increase in maximal blood pressure, etc. corresponding to changes in the user's body due to the identified result. The processor may be configured to suggest a recommended activity for normalizing a change in the user's biological state caused by caffeine intake.

Figure 6A:
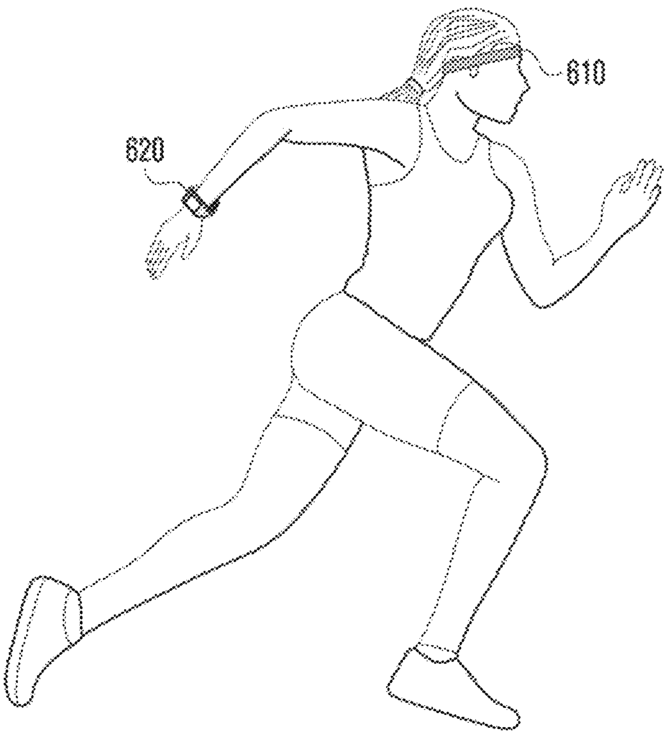
FIGS. 6A and 6B illustrate an example of a method of receiving health care data from an external device according to one or more embodiments.
Figure 6B:

FIGS. 6A and 6B are diagrams illustrating an example of a method of receiving health care data from an external device according to one or more embodiments.

Referring to FIG. 6A, it may show an example in which a user of an electronic device wears an external device (e.g., a smart hairband 610 and a smart watch 620) and performs an activity (e.g., running).

According to an embodiment, the electronic device user may utilize an external device separate from the electronic device, which is connected to the electronic device to transmit and receive data to and from the electronic device. According to another embodiment, the electronic device user may utilize an external device, which is connected to the electronic device to transmit and receive data to and from the electronic device, together with the electronic device. The external devices 610 and 620 may be wearable devices.

Among the wearable devices, the smart hairband 610 may collect first data related to EEG of the electronic device user in a non-invasive way. According to another embodiment, the smart hairband 610 may collect first data in an invasive way.

According to an embodiment, the smart watch 620 may collect a variety of first data such as a heart rate, a pulse rate, a footstep, etc. of the electronic device user. The first data capable of being collected by the smart watch 620 is not limited to the above examples and may further include any information capable of being collected from sensors that may constitute the smart watch.

Referring to FIG. 6B, it may show an example in which a user of an electronic device wears an external device (e.g., a smart clothing 630) and performs an activity.

According to an embodiment, the electronic device user may utilize an external device separate from the electronic device, which is connected to the electronic device to transmit and receive data to and from the electronic device. According to another embodiment, the electronic device user may utilize an external device, which is connected to the electronic device to transmit and receive data to and from the electronic device, together with the electronic device. The external device 630 may be a wearable device. Among the wearable devices, the smart clothing 630 may be equipped with one or more sensors capable of detecting biometric information (e.g., body temperature, heart rate, blood pressure, blood flow, etc.) of the electronic device user. According to another embodiment, first data of the electronic device user detected and/or collected from the smart clothing 630 may be transmitted to the electronic device.

According to an embodiment, the smart clothing 630 may be worn on the electronic device user as a top and/or bottom. According to another embodiment, the smart clothing 630 may include a wide range of clothing and thus encompass equipment such as a hat, shoes, and the like corresponding to wearable devices. The examples of the smart clothing is only an embodiment and may include any wearable device that is in close contact with the body of the electronic device user and performs sensing through a sensor.

Figure 7:
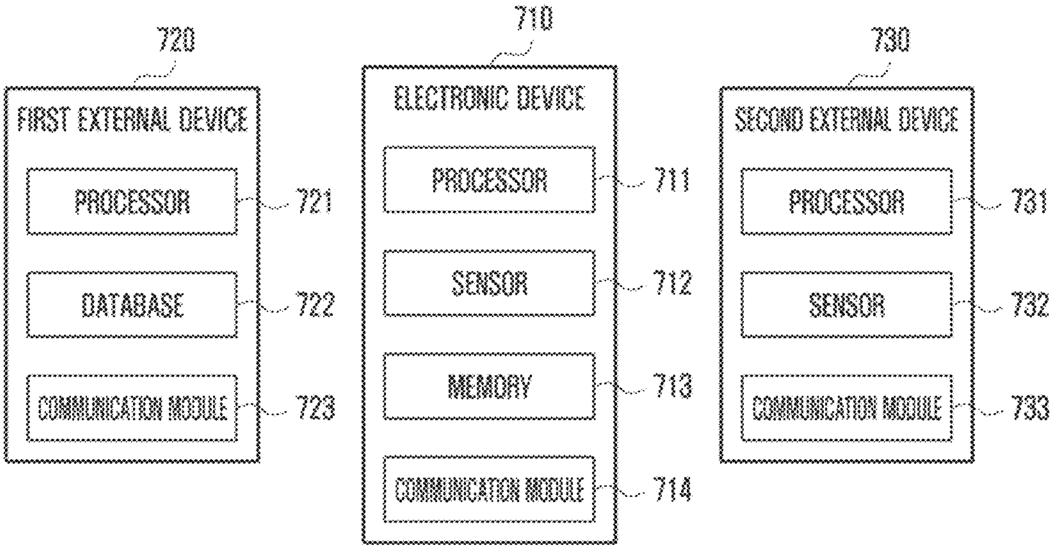
FIG. 7 is a block diagram of an electronic device and external devices for transmitting and receiving health care data according to one or more embodiments.

FIG. 7 is a block diagram of an electronic device and external devices for transmitting and receiving health care data according to one or more embodiments.

Referring to FIG. 7, an electronic device 710, a first external device 720, and a second external device 730 may be connected through communication. For example, a communication module 714 of the electronic device, a communication module 723 of the first external device, and a communication module 733 of the second external device may be connected to each other through wireless communication. The devices connected through communication may be configured to transmit and receive data to and from each other.

The electronic device 710 (e.g., the electronic device 101 in FIG. 1, the electronic device 200 in FIG. 2, or the electronic device 310 in FIG. 3) may include a processor 711, a sensor 712, and a memory 713, and a communication module 714, and some of the illustrated elements may be omitted or substituted. The electronic device may include at least some of the configurations and/or functions of the electronic device 101 in FIG. 1, the electronic device 200 in FIG. 2, and/or the electronic device 310 in FIG. 3.

The processor 711 is an element capable of performing an operation or data processing related to control and/or communication of elements of the electronic device, and may include at least some of the configurations and/or functions of the processor 120 in FIG. 1 and/or the processor 210 in FIG. 2. The processor 711 may be functionally, operatively, and/or electrically connected to elements inside the electronic device, including the sensor 712, the memory 713, and the communication module 714.

The processor 711 may collect and receive user's biometric information sensed by the sensor 712 or biometric information collected or diagnosed by the external device. The information collected described above may be referred to as first data. The user's biometric information capable of being sensed by the sensor 712 may be a heart rate, stress, the number of steps, and the like. The biometric information diagnosed or collected by an external device may be received from a wearable device, a medical diagnostic device, or the like. In this case, the external device may be the second external device 730, and may diagnose or collect biometric information necessary to detect the health state of the user of the electronic device 710. The processor 711 of the electronic device may be configured to receive first data from the second external device 730 using the communication module 714.

The sensor 712 may sense the health state of the electronic device user. For example, the sensor 712 may include a biometric sensor, a temperature sensor, a humidity sensor, and the like. The element of sensor 220 may be omitted or substituted, and may include at least some of the configurations and/or functions of the sensor module 176 in FIG. 1 and/or the sensor 220 in FIG. 2.

The memory 713 may be functionally, operatively, and/or electrically connected to the processor and store one or more instructions capable of being executed by the processor. The instructions may include one or more control commands including arithmetic and logical operations, data transfer, and input/output that may be recognized by the processor. The memory according to one or more embodiments of the disclosure may include at least some of the configurations and/or functions of the memory 130 in FIG. 1 and/or the memory 230 in FIG. 2.

The communication module 714 according to one or more embodiments may support performing communication, including a wireless communication channel, for data sharing between the electronic device and the external devices. The communication module may be operated independently of the processor, or may be connected thereto and operated together, and may include at least some of the structures and/or functions of the communication module 190 in FIG. 1 and/or the communication module 240 in FIG. 2.

The first external device 720 (e.g., the server 108 in FIG. 1) may include a processor 721, a database 722, and a communication module 723, and some of the illustrated elements may be omitted or substituted. The first external device may be a server or may be a server configured as a cloud system. For example, the first external device may update guide information according to a health state by collecting data of respective electronic device users. Here, the guide information may indicate the information produced according to a detected health state of the electronic device user. Only the guide information suitable for the respective electronic device users may be selected from recommended guide information, updated and produced in the first external device, and transmitted, or recommended guide information produced by averaging may be transmitted, or only recommended guide information conforming to an individual electronic device user may be transmitted.

Referring to FIG. 7, the processor 721 of the first external device 720 may be referred to as a second processor to be distinguished from the processor 711 of the electronic device and the processor 731 of the second external device. For example, the processor 711 of the electronic device may be referred to as a first processor, the processor 721 of the first external device may be referred to as a second processor, and the processor 731 of the second external device may be referred to as a third processor so as to be distinguished from each other.

The second processor (e.g., the processor 721 of the first external device) may be configured to store first data and second data of respective users received from a plurality of electronic devices in the database 722. For example, first data and second data accumulated by users of a plurality of electronic devices may be received. At this time, the second processor may be configured to update and produce a variety of recommended guide information according to one or more criteria such as age, gender, type of disease, location information of each user, based on the plurality of pieces of received first and second data.

The database 722 may be functionally, operatively, and/or electrically connected to the processor 721 and store one or more instructions capable of being executed by the processor. The instructions may include one or more control commands including arithmetic and logical operations, data transfer, and input/output that may be recognized by the processor. The database 722 (e.g., memory) according to one or more embodiments of the disclosure may include at least some of the configurations and/or functions of the memory 130 in FIG. 1.

The communication module 723 according to one or more embodiments may support performing communication, including a wireless communication channel, for data sharing between the electronic device and the external devices. The communication module may be operated independently of the processor, or may be connected thereto and operated together, and may include at least some of the structures and/or functions of the communication module 190 in FIG. 1.

Referring to FIG. 7, the communication module 723 of the first external device 720 will be referred to as a second communication module to be distinguishes from the communication module 714 of the electronic device and the communication module 733 of the second external device. For example, the communication module 714 of the electronic device may be referred to as a first communication module, the communication module 723 of the first external device may be referred to as a second communication module, and the communication module 733 of the second external device may be referred to as a third communication module so as to be distinguished from each other.

The second external device 730 (e.g., the electronic device 104 in FIG. 1) may include a processor 731, a sensor 732, and a communication module 733, and some of the illustrated elements may be omitted or substituted. The second external device may be a wearable device, a medical diagnostic device, or a server and include a device capable of collecting biometric information of the electronic device user.

The third processor (e.g., the processor 731 of the second external device) may be configured to collect or diagnose the user's biometric information sensed by the sensor 732. The information collected or diagnosed described above may be referred to as first data. The user's biometric information capable of being sensed by the sensor 732 may be EEG-related information, heart rate, electrocardiogram, the amount of body fluid, blood sugar level, blood oxygen concentration, blood carbon dioxide concentration, and the like. The first data may include all biometric information capable of being collected or diagnosed by a wearable device, a medical diagnostic device, and the like. The processor 731 of the second external device may be configured to transmit the first data to the electronic device 710 using the communication module 733.

The sensor 732 may sense a health state of the electronic device user. For example, the sensor 732 may refer to a sensor included in a wearable device, a medical diagnostic device, or the like.

The communication module 733 according to one or more embodiments may support performing communication, including a wireless communication channel, for data sharing between the second external device and the electronic device 710. The communication module may be operated independently of the processor, or may be connected thereto and operated together, and may include at least some of the structures and/or functions of the communication module 190 in FIG. 1.

Figure 8A:
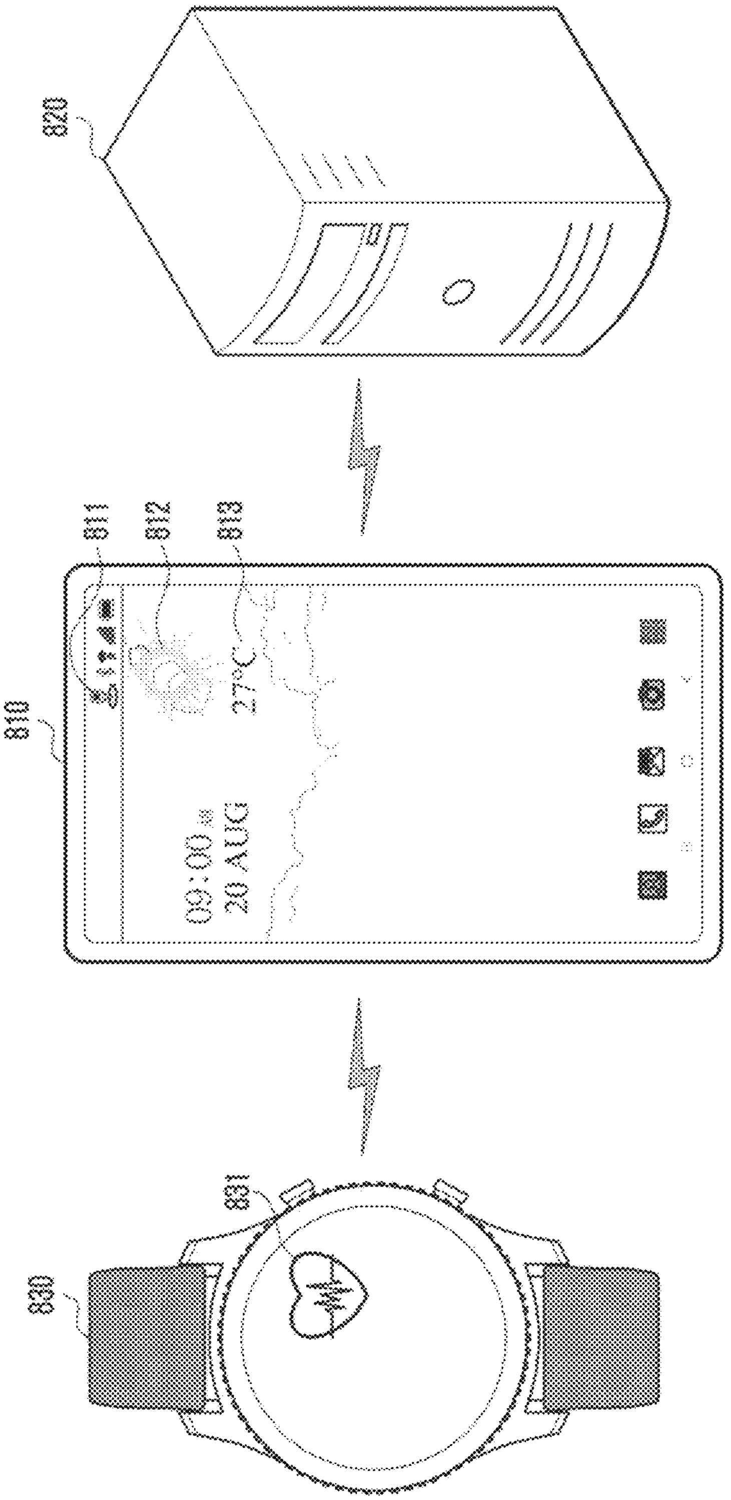
FIGS. 8A and 8B illustrate an example of providing recommended guide information according to a health state of a user of an electronic device.
Figure 8B:
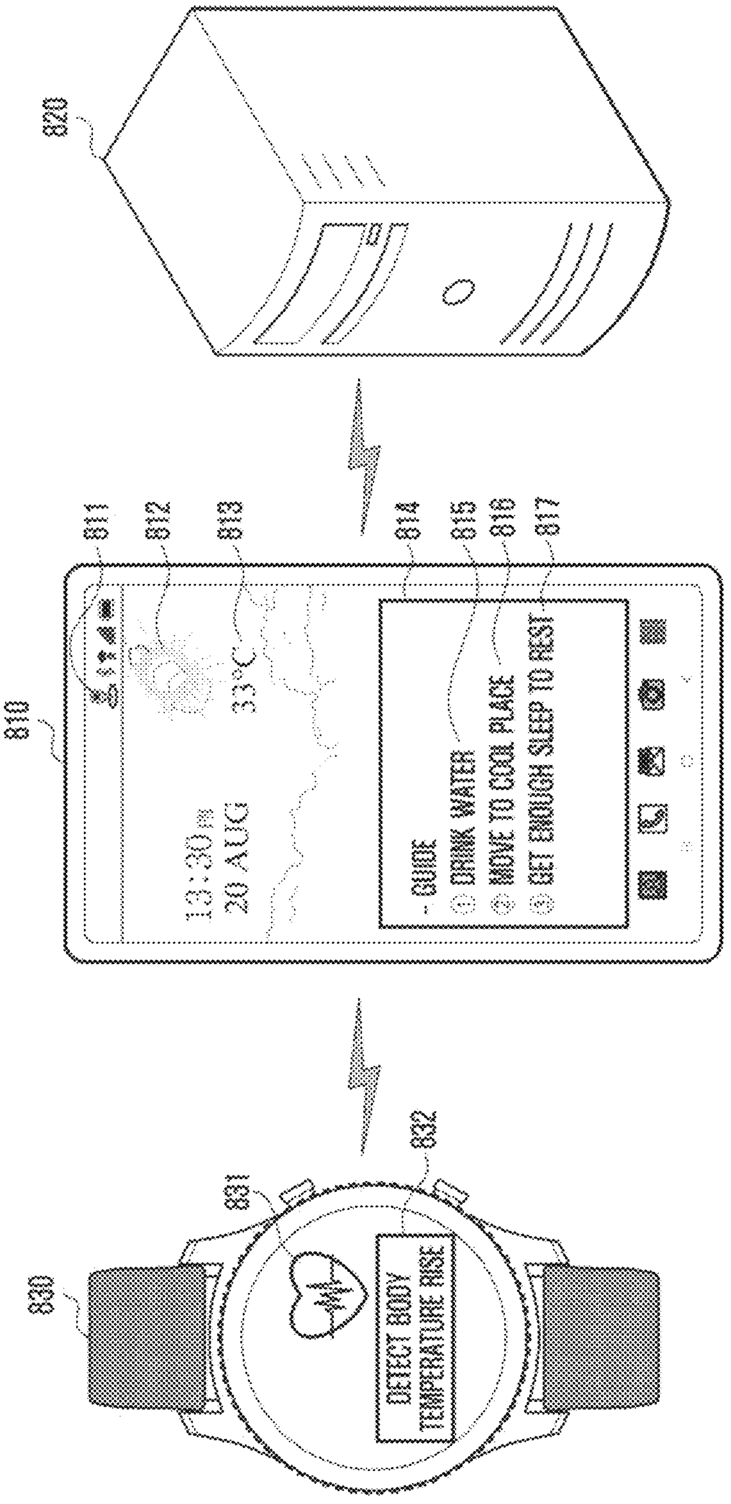

FIGS. 8A and 8B are diagrams illustrates an example of providing recommended guide information according to a health state of a user of an electronic device.

Referring to FIGS. 8A and 8B, an electronic device 810, a first external device 820, and a second external device 830 may be connected to each other through communication. The electronic device 810 may include at least some of the configurations and/or functions of the electronic device 101 in FIG. 1, the electronic device 200 in FIG. 2, the electronic device 310 in FIG. 3, and/or the electronic device 710 in FIG. 7. The electronic device may sense biometric information of an electronic device user through a sensor provided therein and collect a variety of data including the same.

A screen displayed on a display of the electronic device 810 in FIG. 8A (e.g., the electronic device 101 in FIG. 1, the electronic device 200 in FIG. 2, the electronic device 310 in FIG. 3, or the electronic device 710 in FIG. 7) may be a home wallpaper. For example, information 811 about a real-time location where the electronic device user is currently staying may be collected and input as second data. In addition, information 812 about the weather at the real-time location of the user may be collected and input as second data. Information 813 about the temperature at the real-time location of the user may also be collected and input as second data. According to another embodiment, the user's age, gender, chronic disease (e.g., a disease the user has suffered from, a disease the user is suffering from), blood pressure level, or the like, which is information directly input by the electronic device user, may be input as second data.

The first external device 820 in FIG. 8A (e.g., the server 108 in FIG. 1, the external device 330 in FIG. 3, or the first external device 720 in FIG. 7) may include a server. For example, the first external device may collect information about users of a plurality of electronic devices, update guide information corresponding to health states, and provide the same to the plurality of electronic devices. Detecting the health state of the electronic device user and providing guide information may be performed in the electronic device, and the provided guide information may include action rules (e.g., recommended actions), based on the detected health state, that enable the user to return to a normal range. According to an embodiment, if the detected health state of the user indicates dehydration, a message of recommending water intake may be provided from the guide information in the electronic device. In this case, the electronic device may provide the guide information, the external device may provide the guide information, or both devices may provide the guide information.

The second external device 830 in FIG. 8A (e.g., the electronic device 104 in FIG. 1 or the second external device 730 in FIG. 7) may include a wearable device, a medical diagnostic device, or a server. For example, the second external device may include a device for sensing or collecting biometric information of the electronic device user. The user's biometric information may include information on heart rate, electrocardiogram, stress index, number of steps, blood sugar level, amount of body fluid, etc., and include information obtained by quantifying biometric information of the user carrying the electronic device for comparison. According to an embodiment, the second external device may sense a heart rate 831 of the electronic device user and communicate with the electronic device 810 to transmit first data related to the sensed heart rate to the electronic device.

Referring to FIG. 8B, recommended guide information 814 may be provided to the display of the electronic device 810. For example, it may be seen that the temperature shown in FIG. 8B is 33 degrees C., which is higher than the temperature of 27 degrees C. shown in FIG. 8A. The processor of the electronic device 810 identifying the changed second data may provide recommended guide information 814. The recommended guide information may be pre-stored in the memory of the electronic device or received from the first external device 820.

In the case where the body temperature is able to be sensed through the sensor of the second external device 830, display 832 indicating that a body temperature rise was sensed may be displayed. The sensed user biometric information of the electronic device 810 may be transmitted, as first data, to the electronic device and utilized to provide the recommended guide information 814 by the electronic device.

The recommended guide information 814 may be provided to the electronic device user 810 in one or more ways, and is not limited to the examples 815 to 817 shown in FIG. 8B. Referring to FIG. 8B, since the body temperature of the user of the electronic device 810 and the second external device 830 has risen, recommended guide information such as hydration 815, movement to a shaded area 816, and sleep for rest 817 may be provided.

According to another embodiment, the second external device 830 may be a medical device for EEG diagnosis. The medical device for EEG diagnosis may provide EEG information of the user of the electronic device 810 and biometric information of the user of the electronic device 810 obtained by analyzing the EEG information to the electronic device 810. The processor of the electronic device 810 may be configured to compare the received first data (e.g., the user's biometric information obtained by analyzing the EEG information) with a pre-stored threshold value and, if the user's health state falls outside of a threshold value range, provide recommended guide information.

According to one or more embodiments, the recommended guide information 814 may also be referred to as guide information. The recommended guide information may include, for example, countermeasure information according to one or more criteria that may be included in the first data and the second data. According to an embodiment, the recommended guide information may include guide information related to the user's health state obtained from EEG information among the first data. EEG information may be collected by an external device, and the collected EEG information may be compared with a threshold value pre-stored in the electronic device, and if it falls outside of a normal range, guide information such as "take rest", "get enough sleep to rest", and the like may be provided. According to another embodiment, the recommended guide information may include guide information related to the real-time location of the user, among the second data. Guide information such as "move to a cool place", "take a break at a nearby rest area", and the like may be provided according to the real-time location of the user obtained from real-time location information collected from the electronic device and the temperature at the location.

According to one or more embodiments, the recommended guide information may be provided based on a plurality of pieces of first data and second data. For example, guide information may be provided based on information on the current body temperature of the user, among the first data, and information on the age and disease of the user, among the second data. If the current body temperature of the user is 38 degrees C. and if the user is in their early 40's and is currently catching a cold, the processor of the electronic device may provide recommended guide information such as "take enough rest", "take your medicine and go to sleep", "take a fever reducer", and the like.

According to one or more embodiments, the recommended guide information may be produced and provided by the electronic device. In addition, the recommended guide information may be produced by collecting first data and second data of a plurality of users of a plurality of electronic devices by an external device (e.g., a server or a cloud system). According to an embodiment, the recommended guide information capable of being produced by the electronic device and/or the external device may include information enabling the user of the electronic device to remain in the best health state. According to another embodiment, the recommended guide information may have categories provided according to information corresponding to threshold values capable of being pre-stored in a plurality of electronic devices.

According to one or more embodiments, the threshold value pre-stored in the electronic device may relate to a plurality of values. In addition, the threshold values may be updated by being received from an external device and include information updated from an intelligent server. According to an embodiment, the processors included in the plurality of electronic devices may include coprocessors, and the coprocessor may process artificial intelligence models. In addition, the coprocessor may update information on threshold values and/or recommended guide information by utilizing a neural network system.

An electronic device according to one or more embodiments of the disclosure may include a sensor, a memory, and a first processor operatively connected to the sensor and the memory, wherein the first processor may be configured to receive first data of a user of the electronic device sensed at preconfigured intervals using the sensor, identify second data including location information of the user or information input by the user, compare the first data and the second data with threshold values pre-stored in the memory, detect a current health state of the user according to the comparison result, produce recommended guide information pre-stored in the memory according to the detected health state, and repeatedly detect the health state of the user further based on changed first data received at the preconfigured intervals and the second data.

The first data of the electronic device according to one or more embodiments of the disclosure may include biometric information of the user, and the biometric information may include at least one of a heart rate, an electrocardiogram, stress, and a number of steps.

The second data of the electronic device according to one or more embodiments of the disclosure may include at least one of a real-time location of the user, weather at the location, a temperature at the location, and body information of the user.

The electronic device according to one or more embodiments of the disclosure may further include a first communication module, and the first processor may be configured to receive data transmitted from a first external device using the first communication module and store the same in the memory, and update and store data related to the threshold values and the recommended guide information, among the received data.

The first processor of the electronic device according to one or more embodiments of the disclosure may perform comparison with the threshold values pre-stored in the memory further based on at least one of EEG information, blood glucose level information, and blood oxygen concentration of the user transmitted from a second external device using the first communication module.

In the electronic device according to one or more embodiments of the disclosure, the first external device may include a server, and the second external device may include a wearable device, a medical diagnostic device, or a server.

In the electronic device according to one or more embodiments of the disclosure, the first external device may include a second communication module, a database, and a second processor connected to the second communication module and the database, and the second processor may be configured to receive the first data and the second data from the electronic device using the second communication module, store the received first data and second data in the database, update the guide information for the user of the electronic device, based on information of the database, and transmit the updated guide information to the electronic device using the second communication module.

A method of operating an electronic device according to one or more embodiments of the disclosure may include receiving first data of a user of the electronic device sensed at preconfigured intervals using a sensor, identifying second data including location information of the user or information input by the user, comparing the received first data and the identified second data with threshold values pre-stored in a memory, detecting a current health state of the user according to the comparison result, producing recommended guide information pre-stored in the memory according to the detected health state, and re-detecting the health state of the user further based on changed first data received at the preconfigured intervals and the second data.

In the method of operating an electronic device according to one or more embodiments of the disclosure, the receiving may include receiving biometric information, as first data, including at least one of a heart rate, an electrocardiogram, stress, and a number of steps of the user.

In the method of operating an electronic device according to one or more embodiments of the disclosure, the identifying may include identifying second data including at least one of a real-time location of the user, weather at the location, a temperature at the location, and body information of the user.

The method of operating an electronic device according to one or more embodiments of the disclosure may include receiving data transmitted from a first external device using a first communication module and storing the same in the memory, and updating and storing data related to the threshold values and the recommended guide information, among the received data.

In the method of operating an electronic device according to one or more embodiments of the disclosure, the comparing may include performing comparison with the threshold values pre-stored in the memory further based on at least one of EEG information, blood glucose level information, and blood oxygen concentration of the user transmitted from a second external device using the first communication module.

In the method of operating an electronic device according to one or more embodiments of the disclosure, the first external device may include a server, and the second external device may include a wearable device, a medical diagnostic device, or a server.

In the method of operating an electronic device according to one or more embodiments of the disclosure, the producing may include receiving the first data and the second data from the electronic device using a second communication module of the first external device, storing the received first data and second data in a database of the first external device, updating the guide information for the user of the electronic device, based on information of the database, receiving the updated guide information using the first communication module, and producing the guide information, based on the updated guide information.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as “A or B,” “at least one of A and B,” “at least one of A or B,” “A, B, or C,” “at least one of A, B, and C,” and “at least one of A, B, or C,” may include any one of, or all possible combinations of the items enumerated together in a corresponding one of the phrases. As used herein, such terms as “1st” and “2nd,” or “first” and “second” may be used to simply distinguish a corresponding component from another, and does not limit the components in other aspect (e.g., importance or order). It is to be understood that if an element (e.g., a first element) is referred to, with or without the term “operatively” or “communicatively,” as “coupled with,” “coupled to,” “connected with,” or “connected to” another element (e.g., a second element), it means that the element may be coupled with the other element directly (e.g., wiredly), wirelessly, or via a third element.

As used in connection with various embodiments of the disclosure, the term “module” may include a unit implemented in hardware, software, or firmware, and may interchangeably be used with other terms, for example, “logic,” “logic block,” “part,” or “circuitry.” A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities, and some of the multiple entities may be separately disposed in different components. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

What is claimed is:

1. A wearable electronic device comprising:

a sensor configured to sense biometric information of a user at preconfigured intervals;

memory configured to store threshold values and executable instructions;

a display; and a first processor operably coupled to the sensor, memory, and display, the first processor comprising software modules configured to execute a set of instructions stored in the memory to:

control the sensor to automatically measure the biometric information of the user at the preconfigured intervals;

obtain, from the sensor, the biometric information of the user measured by the sensor at the preconfigured intervals, the biometric information including heart rate, an electrocardiogram, stress level, and a number of steps;

quantify the biometric information of the user measured by the sensor into first data, the first data being at least one of electroencephalography (EEG) information including sensorimotor rhythm, regional cerebral blood flow, levels of neurotransmitter, heart rate, stress level, blood pressure, blood oxygen concentration, or a blood carbon dioxide concentration;

identify, via processor, second data comprising at least one of a location information of the user or user-inputted information;

compare the first data and the second data with threshold values pre-stored in the memory to generate a result, using a predefined learning algorithms and signal processing techniques, the threshold values being values indicating normal ranges of biometric information statistically based on user information;

detect a current health state of the user based on the result, the current health state of the user being a mental state classification label of the user;

control the display to output recommended guide information according to the detected current health state to the user, the recommended guide information including at least one of guide information for physical activity to enable alteration of EEG, alteration of blood flow to a first normal range, or alteration of blood oxygen concentration to a second normal range;

re-detect the current health state of the user based on changed first data obtained by quantifying changed biometric information measured at the preconfigured intervals and the second data, the changed first data being at least one of EEG information including sensorimotor rhythm, regional cerebral blood flow, levels of neurotransmitter, heart rate, stress level, blood pressure, blood oxygen concentration, or blood carbon dioxide concentration, and the current health state of the user being the mental state classification label of the user;

transmit the first data and the second data to an external device using a communication module, to enable the external device to generate updated recommended guide information, based on the first data, the second data, and a plurality of other pieces of data for other users having similar characteristics to the user of the wearable electronic device received from a plurality of other electronic devices associated with the other users;

receive the updated recommended guide information from the external device, the updated recommended guide information including at least one of guide information for physical activity to enable alteration of EEG, alteration of blood flow to the first normal range, or alteration of blood oxygen concentration to the second normal range; and control the display to output guide information included in the updated recommended guide information received from the external device, that is determined to be applicable to the current health state of the user based on the changed first data, and the second data, wherein the updated recommended guide information comprises recommendations to the user based on aggregated habit-related data of the other users of the plurality of other electronic devices.

2. The wearable electronic device of claim 1, wherein the second data comprises at least one of a real-time location of the user, weather at the location, a temperature at the location, and body information of the user.

3. The wearable electronic device of claim 1, further comprising:

a first communication module, wherein the first processor is further configured to:

receive data of the plurality of other pieces of data transmitted from a first external device of the plurality of other electronic devices via the first communication module and store the received data in the memory; and update and store the received data related to the threshold values and the recommended guide information.

4. The wearable electronic device of claim 3, wherein the first processor is further configured to:

compare the threshold values pre-stored in the memory based on at least one of EEG information, blood glucose level information, and blood oxygen concentration of the user transmitted from a second external device of the plurality of other electronic devices via the first communication module.

5. The wearable electronic device of claim 4, wherein the first external device comprises a server, and wherein the second external device comprises a wearable device, a medical diagnostic device, or a server.

6. The wearable electronic device of claim 3, wherein the first external device comprises:

a second communication module;

a database; and a second processor connected to the second communication module and the database, and wherein the second processor is configured to:

receive the first data and the second data from the wearable electronic device via the second communication module;

store the first data and the second data in the database;

update the guide information for the user of the wearable electronic device, based on information of the database; and transmit the updated guide information to the wearable electronic device via the second communication module.

7. A method of operating a wearable electronic device, the method comprising:

continuously measuring, via a sensor, biometric information of a user of the wearable electronic device at preconfigured intervals, the biometric information including heart rate, an electrocardiogram, stress level, and a number of steps;

quantifying the biometric information of the user measured by the sensor as first data, the first data being at least one of electroencephalography (EEG) information including sensorimotor rhythm, regional cerebral blood flow, levels of neurotransmitter, heart rate, stress level, blood pressure, blood oxygen concentration, or blood carbon dioxide concentration;

identifying, via a processor comprising executable software modules implemented on the processor, second data comprising at least one of a location information of the user or user inputted information;

comparing the first data and the second data with threshold values pre-stored in memory to generate a result, using a predefined learning algorithms and signal processing techniques, the threshold values being values indicating normal ranges of biometric information statistically based on user information;

based on the comparing, detecting a current health state of the user, the current health state of the user being a mental state classification label of the user;

outputting recommended guide information according to the detected current health state to the user via a display of the wearable electronic device, the recommended guide information including at least one of guide information for physical activity to enable alteration of EEG, alteration of blood flow to a first normal range, or alteration of blood oxygen concentration to a second normal range;

re-detecting the current health state of the user based on changed first data obtained by quantifying changed biometric information measured at the preconfigured intervals and the second data, the changed first data being at least one of EEG information including sensorimotor rhythm, regional cerebral blood flow, levels of neurotransmitter, heart rate, stress level, blood pressure, blood oxygen concentration, or blood carbon dioxide concentration, and the current health state of the user being the mental state classification label of the user;

transmitting the first data and the second data to an external device using a communication module, to enable the external device to generate updated recommended guide information, based on the first data, the second data, and a plurality of other pieces of data for other users having similar characteristics to the user of the wearable electronic device received from a plurality of other electronic devices associated with the other users, the plurality of other electronic devices being at least one of a smart hairband, a smartwatch, or smart clothing being at least one of a smart hat, smart shoes, a smart top, or a smart bottom;

receiving the updated recommended guide information from the external device, the updated recommended guide information including at least one of guide information for physical activity to enable alteration of EEG, alteration of blood flow to the first normal range, or alteration of blood oxygen concentration to the second normal range; and outputting, via the display, guide information included in the updated recommended guide information received from the external device that is determined to be applicable to the current health state of the user based on the changed first data, and the second data, wherein the updated recommended guide information comprises recommendations to the user based on aggregated habit-related data of the other users of the plurality of other electronic devices.

8. The method of claim 7, wherein the identifying comprises:

identifying second data comprising at least one of a real-time location of the user, weather at the location, a temperature at the location, and body information of the user.

9. The method of claim 7, further comprising:

receiving data of the plurality of other pieces of data transmitted from a first external device of the plurality of other electronic devices via a first communication module and storing the same in the memory; and updating and storing data related to the threshold values and the recommended guide information, among the received data.

10. The method of claim 9, wherein the comparing comprises performing comparison with the threshold values pre-stored in the memory further based on at least one of EEG information, blood glucose level information, and blood oxygen concentration of the user transmitted from a second external device of the plurality of other electronic devices via the first communication module.

11. The method of claim 10, wherein the first external device comprises a server, and wherein the second external device comprises a wearable device, a medical diagnostic device, or a server.

12. The method of claim 9, the outputting comprises:

receiving the first data and the second data from the wearable electronic device via a second communication module of the first external device;

storing the first data and the second data in a database of the first external device;

updating the guide information for the user of the wearable electronic device, based on information of the database;

receiving the updated guide information via the first communication module; and outputting the guide information, based on the updated guide information.

* * * * *